United States Patent [19]

Dressler et al.

[11] Patent Number: 4,645,780

[45] Date of Patent: Feb. 24, 1987

[54] NOVEL BIOCIDES EMPLOYING RESORCINOL DERIVATIVES

[75] Inventors: Hans Dressler, Monroeville; Hans A. Ward, New Kensington, both of Pa.

[73] Assignee: Koppers Company, Inc., Pittsburgh, Pa.

[21] Appl. No.: 817,984

[22] Filed: Jan. 13, 1986

[51] Int. Cl.$^4$ .................... A01N 31/08; A01N 57/00
[52] U.S. Cl. ....................................... 514/731; 514/130
[58] Field of Search ............................... 514/731, 492

[56] References Cited

U.S. PATENT DOCUMENTS 4,219,570  8/1980  Inazuka ............................... 514/731

FOREIGN PATENT DOCUMENTS 927255  5/1963  United Kingdom ................ 514/731
933684  8/1963  United Kingdom ................ 514/731

*Primary Examiner*—Allen J. Robinson
*Attorney, Agent, or Firm*—Daniel J. Long; Herbert J. Zeh, Jr.

[57] ABSTRACT

A method of protecting organic materials from fungi and/or bacteria is provided which comprises applying to said organic material a minor but effective biocidal amount of a compound of the formula:

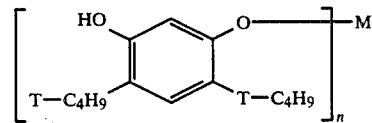

wherein M is selected from H,P and an alkali metal or alkali earth metal and n is an integer selected from 1 to 3.

6 Claims, No Drawings

NOVEL BIOCIDES EMPLOYING RESORCINOL DERIVATIVES

BACKGROUND OF THE INVENTION

Many organic materials are subject to degradation due to fungal or bacterial attack. For example, wood is one of the best structural materials for the construction of buildings because of its strength, ease of processing, and relatively low cost, but wood has one serious drawback in that it is susceptible to discoloration and decay by wood destroying fungi. While there are a number of materials that will control bacteria and fungi, many are highly toxic to man. This invention is directed to compounds that are both effective biocides and also of low toxicity to man.

BRIEF DESCRIPTION OF THE INVENTION

This invention relates to a biocide (i.e. bactericide or fungicide) for preservative compositions useful for application in wood, paint, fuels, lubricants and other organic materials. More particularly, this invention relates to a biocide comprising as its essential ingredient a compound of the formula:

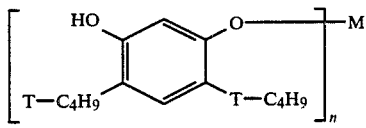

wherein M is selected from H,P or an alkali metal or alkali earth metal and n is an integer selected from 1 to 3. The preferred alkali metals are sodium and potassium but lithium, rubidium and cesium may also be employed. Any of calcium, strontium and barium may be employed as alkali earth metals. When M is P, n is 3 and when M is H or an alkali metal, then M is 1 and when M is an alkali earth metal, then M is 2.

4,6-Di-t-butylresorcinol is a known compound. The salts are prepared by reaction of the metal oxide or hydroxide with dibutylresorcinol in a suitable solvent (e.g. water, an alcohol or an alkoxyalkanol or a dihydric alcohol optionally in the presence of water) and used as is or stripped of solvent to make a dry salt which can be redispersed. Tris-(3-hydroxy-4,6-di-t-alkylphenyl)-phosphite can be made from 4,6-di-t-butylresorcinol and phosphorus trichloride in the presence of pyridine, alkylpyridines, quinolines or aryl phosphines as the catalyst and aliphatic or aromatic hydrocarbons or halogenated hydrocarbons as the solvent.

DETAILED DESCRIPTION OF THE INVENTION

The biocide compositions of the invention can be prepared as solutions or emulsions by conventional means using water or organic solvents, or the neat materials can be used without solvents.

The quantity of biocide will depend upon the specific application. Generally, however, the preservative will contain from about 0.01 to 100% by weight biocide and preferably from about 0.1 to about 5% by weight biocide would be used. If a solvent is used it will generally comprise from about 90 to about 99% by weight of the total preservative composition. Typical solvents include water, aromatic solvents such as xylene and toluene, alcohols such as methanol, ethanol and hexanol, ketones such as acetone, cyclohexanone and diisobutylketone, aliphatic solvents such as pentane, hexane and mineral spirits, and mixtures.

If desired, the preservative may incorporate other preservatives. Typical preservatives include pentachlorophenol, zinc naphthenate, copper naphthenate and the like.

The following examples will serve to illustrate the invention and preferred embodiments thereof. All parts and percentages in said examples and elsewhere in the specification and claims are by weight unless otherwise indicated.

EXAMPLE 1

Ten small red pine wood samples, (10×10×100 mm) were soaked for 30 seconds in 1.0% 4,6-di-t-butylresorcinol (DTBR)/methanol solution. After air drying, the samples were placed in a dish and inoculated with a spore suspension of the mold fungus *Aspergillus niger*. The fungus growth was then measured after 4, 8, and 16 days incubation at 90% relative humidity and 32° C. Untreated control samples and pentachlorophenol-treated samples were included for comparison purposes. The results are shown in the following Table 1.

TABLE 1

| Compounds | Conc. | Average Mold Growth[1] On Coated Wood Samples After | | |
| --- | --- | --- | --- | --- |
| | | 4 days | 8 days | 16 days |
| Pentachlorophenol | 1.0 | −0.1 | −0.1 | −0.1 |
| 4,6-di-t-butyl resorcinol[2] | 1.0 | −0.1 | −0.1 | −0.1 |
| Control | 0 | 10.0 | 10.0 | 10.0 |

[1]Average of 10 samples
Mold: *Aspergillus niger*
Rating of mold growth on the samples: −10 = inhibition zone of 10 mm; 0 = no growth on the samples; 10 = samples covered with growth
[2]$LD_{50}$ = 3.08 g/kg - male rat ingestion
$LD_{50}$ > 2.00 g/kg - male rat skin penetration From the results, it can be seen that DTBR is equal in fungicidal effectiveness to pentachlorophenol, a commercial preservative.

EXAMPLE 2

In the following Table 2 fungicidal activity against wood-destroying fungi was determined as described above in Example I, except birch wood samples were used which were soaked with 1% solutions of DTBR or tris-(3-hydroxy-4,6-di-t-butylphenyl)phosphite of the formula

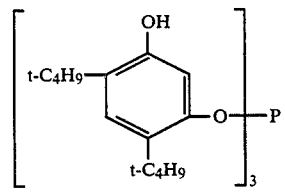

or pentachlorophenol, or a 1% solution of CCA-C(copper-chromium-arsenate) preservative in water. The wood samples were then placed in a dish and inoculated with mycellial suspensions of a mixture of fungi as listed in the footnote to Table II. The test specimens where then incubated for 10 days and 30 days at 90% relative humidity and 32° C.

The results show that DTBR and its derived phosphite are as least as effective, and in some cases more effective, as preservatives as pentachlorophenol and CCA-C.

TABLE 2

| Candidate Preservative | Conc. % | Average Protection Against Brown and White Rot Decay | |
|---|---|---|---|
| | | 10 days | 30 days |
| | | % of Sample Surface Protected | |
| 4,6-di-t-butylresorcinol | 1.0 | 109(2) | 100 |
| tris-(3-hydroxy-4,6-di-t-butylphenyl) phosphite | 1.0 | 109(2) | 100 |
| Pentachlorophenol | 1.0 | 100 | 85 |
| CCA-C | 1.0 | 100 | 100 |
| Control | — | 0 | 0 |

(1)Average of 10 samples. Laboratory bioassay. Test Fungi: *Trichoderma viride, Aspergillus niger, Paecilomyces varioti, Chaetomium globosum, Diplodia natalensis, Gloeophyllum trabeum, Coriolus vesicolor, Poria placenta,* and *Lentinus lepideus.*
(2)Protection greater than 100% indicates an inhibition zone around the samples.

EXAMPLE 3

4,6-di-t-butylresorcinol was evaluated as a wood preservative against a brown-rot decay fungus, as shown in Table 3, using a standard ASTM test D1413-76 soil block test.

Again, DTBR was found to be as effective a preservative as pentachlorophenol.

TABLE 3

Toxic threshold values (pound of chemical per cubic foot of wood or pcf of the active ingredients) of pentachlorophenol and 4,6-di-t butylresorcinol against the brown-rot decay fungus, *Gloeophyllum trabeum.*

| Chemical | Toxic Threshold (Value pcf) |
|---|---|
| Pentachlorophenol | 0.36 (pcf) |
| 4,6-di-t-butyl resorcinol | 0.36 (pcf) |

EXAMPLE 4

In an agar plate test for bactericidal activity, 4,6-di-t-butylresorcinol showed very good activity against gram positive bacteria as shown in Table 4.

TABLE 4

Agar Plate Test for Bactericidal Activity of 4,6-di-t-butylresorcinol

| Test Organism | Lowest ppm Needed To Inhibit Growth |
|---|---|
| *Aspergillus niger* | 100 |
| *Bacillus subtili* | 50 |
| *Staphylococcus aureus* | 100 |

What is claimed is:

1. A method of protecting organic materials from fungi and/or bacteria which comprises applying to said organic material a fungicidally and/or bactericidally effective amount of a compound of the formula:

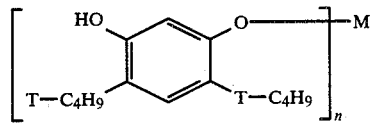

wherein M is H, an alkali metal or alkali earth metal and n is an integer of 1 or 2.

2. The method of claim 1 wherein the compound is 4,6-di-t-butylresorcinol.

3. The method of claim 1 wherein the organic material is wood.

4. The method of claim 1 wherein the compound is contained in a preservative comprising from about 90% to about 99% solvent.

5. The method of claim 1 wherein the compound is contained in a preservative comprising a mixture of solvents comprising from about 90% to about 99% solvent.

6. The method of claim 1 wherein the compound is 4,6-di-t-butylresorcinol and the organic material is wood.

* * * * *